(12) United States Patent
Liu (10) Patent No.: US 10,069,240 B2
(45) Date of Patent: Sep. 4, 2018

(54) ELECTRONIC CIGARETTE (71) Applicant: HUIZHOU KIMREE TECHNOLOGY CO., LTD. SHENZHEN BRANCH, Shenzhen, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 0 days.

(21) Appl. No.: 15/118,502

(22) PCT Filed: Feb. 12, 2014

(86) PCT No.: PCT/CN2014/072003
§ 371 (c)(1),
(2) Date: Aug. 12, 2016

(87) PCT Pub. No.: WO2015/120587
PCT Pub. Date: Aug. 20, 2015

(65) Prior Publication Data
US 2017/0162979 A1    Jun. 8, 2017

(51) Int. Cl.
| | |
|---|---|
| H01R 13/62 | (2006.01) |
| A24F 1/10 | (2006.01) |
| A24F 1/32 | (2006.01) |
| A24F 13/00 | (2006.01) |
| A24F 13/02 | (2006.01) |
| A24F 47/00 | (2006.01) |
| A61M 15/06 | (2006.01) |
| H01M 2/10 | (2006.01) |
| H02J 7/00 | (2006.01) |

(52) U.S. Cl.
CPC ....... *H01R 13/6205* (2013.01); *A24F 47/008* (2013.01); *A61M 15/06* (2013.01); *H01M 2/1022* (2013.01); *H02J 7/0045* (2013.01); *H01M 2/1055* (2013.01); *H01M 2220/30* (2013.01)

(58) Field of Classification Search
CPC .. A24F 47/008; A61M 11/042; A61M 11/044; H01R 13/6205
See application file for complete search history.

(56) References Cited

U.S. PATENT DOCUMENTS

| | | | | |
|---|---|---|---|---|
| 2014/0261493 | A1* | 9/2014 | Smith | A24F 47/008 131/328 |
| 2014/0366896 | A1* | 12/2014 | Li | A24F 47/008 131/329 |

* cited by examiner

Primary Examiner — Alex Efta (57) ABSTRACT

The invention is related to an electronic cigarette comprises an atomizer and a battery rod connected with each other, a first connector and a second connector connect the atomizer and the battery rod, a fastener is arranged on the first connector, a butting groove is arranged on the second connector, a guide groove extending axially of the battery rod and a clamping groove extending circumferentially of the battery rod and communicated with the guide groove are arranged on the sidewall of the butting groove, the fastener is clamped into the clamping groove, a first magnetic member is arranged on the second connector, and a second magnetic member for attracting the first magnetic member to prevent the fastener-from being rotated back into the guiding groove is arranged on the first magnetic member. The electronic cigarette is firm in connection and simple in operation.

3 Claims, 6 Drawing Sheets

ELECTRONIC CIGARETTE

TECHNICAL FIELD

The present application relates to the field of daily electrical products, and more particularly relates to an electronic cigarette.

BACKGROUND

An electronic cigarette is a relatively common simulation electronic cigarette product, mainly comprises tar storage cotton, atomizing assembly and battery. Atomizing assembly is charged by battery, which makes the atomizing assembly generate heat, then vaporize the tobacco tar in the cotton to discharge the gas, thus can achieve the result of the simulation of cigarettes.

Electronic cigarette generally comprises atomizing assembly and battery assembly. In the prior art, electronic cigarette is connected by direct buckling or magnetism, and this kind of simple insertion or magnetic connection way easily results in unstable connection. According to the above defects, in the prior art, the electronic cigarette provides a threaded connection, however this way of connection may exists the following defects: atomizer may rotate back because of shock which results in loose connection, and this connection way is complicated to operate.

BRIEF SUMMARY

In view of the above defects, the present invention provides an electronic cigarette which is firm in connection and simple in operation.

The electronic cigarette in present invention, comprises atomizer and a battery rod which are connected with each other, a first connector and a second connector for connecting the atomizer with the battery rod are arranged at the location where the atomizer and the battery rod are connected with each other, a fastener is arranged on the first connector, a butting groove is arranged on the second connector, a guide groove extending in the axial direction of the battery rod and a clamping groove extending in the circumferential direction of the battery rod and communicated with the guide groove are arranged on the sidewall of the butting groove, the fastener is clamped into the clamping groove, a first magnetic member is further arranged on the second connector, and a second magnetic member for attracting the first magnetic member so as to prevent the fastener from being rotated back into the guiding groove is further arranged on the first connector.

In the electronic cigarette according of the present invention, the atomizer comprises an atomizer electrode assembly, the first connector is the atomizer electrode assembly.

In the electronic cigarette according of the present invention, the battery rod comprises an external battery rod electrode, the second connector is the external battery rod electrode.

In the electronic cigarette according of the present invention, the atomizer electrode assembly comprises an external atomizer electrode, an inner atomizer electrode which is arranged in the external atomizer electrode, and an atomizer insulator ring which is arranged between the external atomizer electrode and the inner atomizer electrode.

In the electronic cigarette according of the present invention, the second magnetic member is the external atomizer electrode.

In the electronic cigarette according of the present invention, the fastener is a first bulge formed by extending from an outside surface of the external atomizer electrode towards a direction of away from a central axis of the external atomizer electrode.

In the electronic cigarette according of the present invention, the first magnetic member is contained in the external battery rod electrode, and encloses with the internal surface of the external battery rod electrode to form the clamping groove.

In the electronic cigarette according of the present invention, the first magnetic member is hollow cylinder, a fastening arm is formed by axially extending form an end surface of the first magnetic member towards the external atomizer electrode, the fastening arm encloses with the internal surface of the external battery rod electrode to form the clamping groove.

In the electronic cigarette according of the present invention, the first magnetic member and the external battery rod electrode form an integrated structure.

In the electronic cigarette according of the present invention, the external battery rod electrode is hollow cylinder, an opening is disposed on the circumference surface of the external battery rod electrode, the first magnetic member is clamped into the opening.

In the electronic cigarette according of the present invention, the shape of the first magnetic member is consistent with the shape of the opening.

In the electronic cigarette according of the present invention, the two ends of the first magnetic part extend towards each other to form backstop bulges, the backstop bulges enclose with the internal surface of the external battery rod electrode to form the clamping groove.

In the electronic cigarette according of the present invention, the second magnetic member is the fastener.

In the electronic cigarette according of the present invention, the fastener is a second bulge formed by extending from an outside surface of the atomizer insulator ring towards the direction of away from the central axis of the atomizer electrode assembly, the fastener protrudes from an outer surface of the external atomizer electrode.

The beneficial effects of the present invention is: the atomizer and the battery rod are connected by clamping the fastener of the first connector into the clamping groove of the second connector, at the same time, the magnetic members made of magnetic material such as magnet, iron, nickel and cobalt are respectively disposed on the first connector and the second connector, so that the atomizer and battery rod can attract with each other during the connection, thus avoiding the atomizer and battery rod being loose to separate, so that the present invention provides an electronic cigarette which is firm in connection and simple in operation and improves the users' experience.

BRIEF DESCRIPTION OF THE DRAWINGS

The present application will be further described with reference to the accompanying drawings and embodiments in the following, in the accompanying drawings.

DETAILED DESCRIPTION OF THE PREFERRED EMBODIMENT

To make the technical feature, objective and effect of the present application be understood more clearly, now the specific implementation of the present application is described in detail with reference to the accompanying drawings and embodiments.

The present application takes the number of the fastener 104, the guide groove 230 and the clamping groove 210 are two as examples, to describe the present application in detail. The design methods of the two fasteners 104, two guide grooves 230 and two clamping grooves 210 should not be understood as absolute limit to scope of protection, the number of the fastener 104, the guide groove 230 and the clamping groove 210 can be other numbers.

Figure 1:
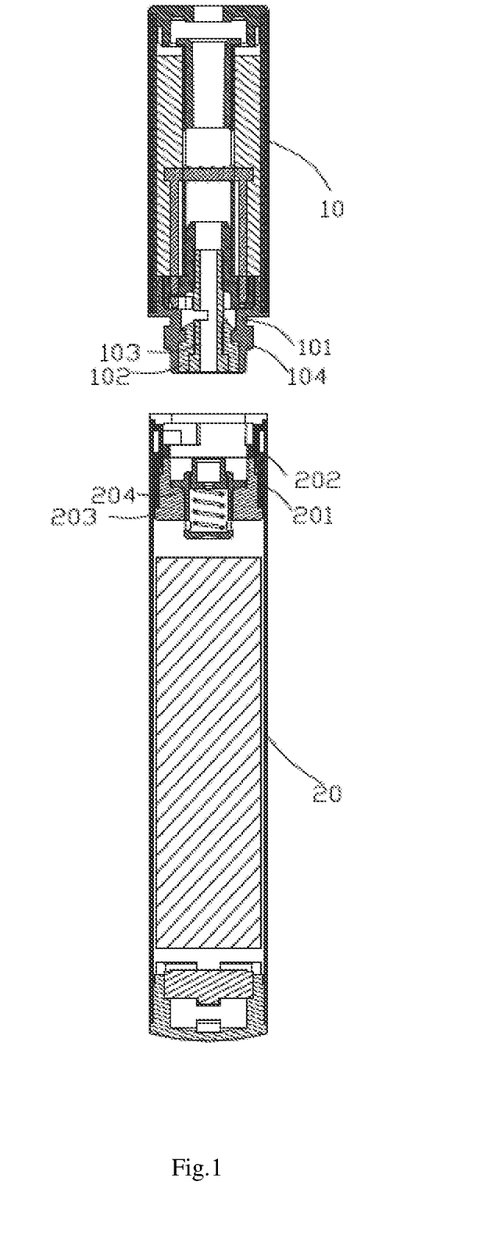
FIG. 1 is a structural schematic view of an electronic cigarette of the present application in a first embodiment.
Figure 2:
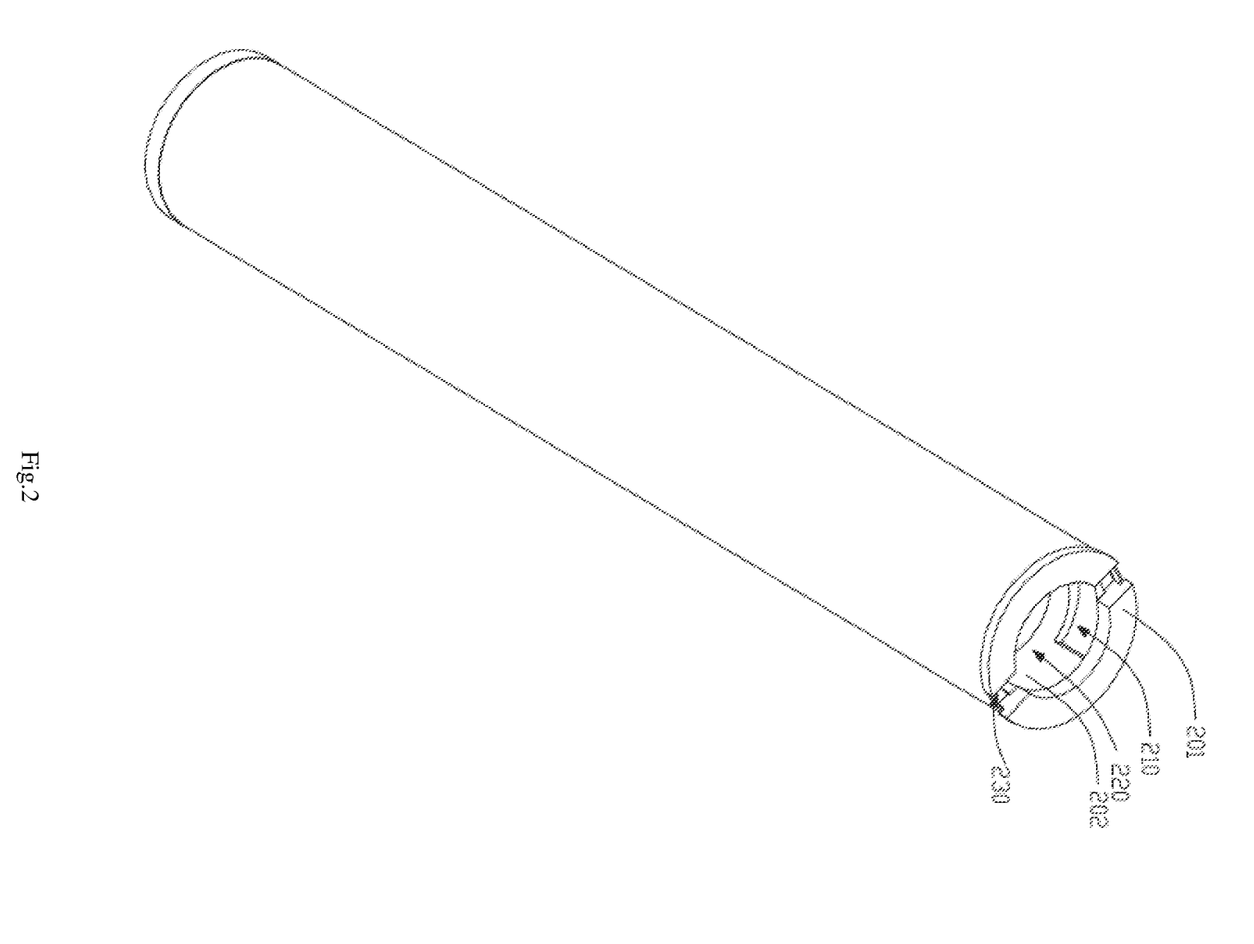
FIG. 2 is a structural schematic view of battery rod shown in FIG. 1.

As shown in FIG. 1-2, a structural schematic view of an electronic cigarette of the present application in a first embodiment. The electronic cigarette comprises an atomizer 10 and a battery rod 20. A first connector and a second connector for connecting the atomizer 10 with the battery rod 20 are arranged at where the atomizer 10 and the battery rod 20 are connected with each other. The atomizer 10 comprises an atomizer sleeve, and an atomizing assembly and a tar storage cotton which are arranged in the atomizer sleeve. The battery rod 20 comprises a battery sleeve and a battery arranged in the battery sleeve. An atomizing electrode assembly and a battery rod electrode assembly are arranged at connection ends of the atomizer 10 and the battery rod 20 respectively. The atomizing electrode assembly comprises a cannular external atomizer electrode 101, a rod-shaped inner atomizer electrode 103 which is arranged in the external atomizer electrode 101, and an atomizer insulator ring 102 which is arranged between the external atomizer electrode 101 and the inner atomizer electrode 103. The atomizer insulator ring 102 is used to electrically insulate the external atomizer electrode 101 from the inner atomizer electrode 103. Correspondingly, The battery rod electrode assembly comprises a cannular external battery rod electrode 201, a rod-shaped inner battery rod electrode 204 which is arranged in the external battery rod electrode 201, and an battery rod insulator ring 203 which is arranged between the external battery rod electrode 201 and the inner battery rod electrode 204. When assembling the electronic cigarette, the atomizer 10 and battery rod 20 are connected by clamping connection between atomizing electrode assembly and battery rod electrode assembly. In this embodiment, the first connector is the atomizing electrode assembly, the second connector is the external battery rod electrode 201. Understandably, in other embodiments, the first connector can be external battery rod electrode 201, and the second connector can be atomizing electrode assembly. Meanwhile, for purpose of stronger connection between the battery rod 20 and the atomizer 10, to prevent the atomizer 10 from being rotated back because of shock after connection, magnetic members made of magnetic material such as magnet, iron, nickel and cobalt are respectively disposed on the first connector and the second connector, so that the atomizer 10 and battery rod 20 can attract with each other during the connection, to prevent the atomizer 10 from being rotated back because of shock, further avoiding the atomizer 10 and battery rod 20 being loose to separate, and improves the users' experience.

Specifically, a fastener 104 is arranged on the first connector, a butting groove 220 is arranged on the second connector. A guide groove 230 extending in the axial direction of the battery rod and a clamping groove 210 extending in the circumferential direction of the battery rod 20 and communicating with the guide groove 230 are arranged on an sidewall of the butting groove 220, the fastener 104 is clamped into the clamping groove. A first magnetic member 202 is further arranged on the second connector, and a second magnetic member for attracting the first magnetic member 202 so as to prevent the fastener 104 from being rotated back into the guiding groove 230 is further arranged on the first connector.

In this embodiment, specifically, the first connector is the external atomizer electrode. The fastener 104 is arranged on the external atomizer electrode 101. The fastener 104 is a first bulge formed by extending from an outside surface of the external atomizer electrode 101 towards the direction of away from the central axis of the external atomizer electrode 101. In order to reduce machining process, and save cost, the fastener 104 and the external atomizer electrode 101 form an integrated structure. In this embodiment, the second magnetic member can be the external atomizer electrode 101, that is the external atomizer electrode 101 is made of magnetic materials such as magnet, iron, or nickel. The advantages of the setting of second magnetic member are as follows: it is unnecessary to add separate magnetic member during the manufacturing process of electronic cigarettes, save the production cost and reduce the processing steps.

Figure 3:
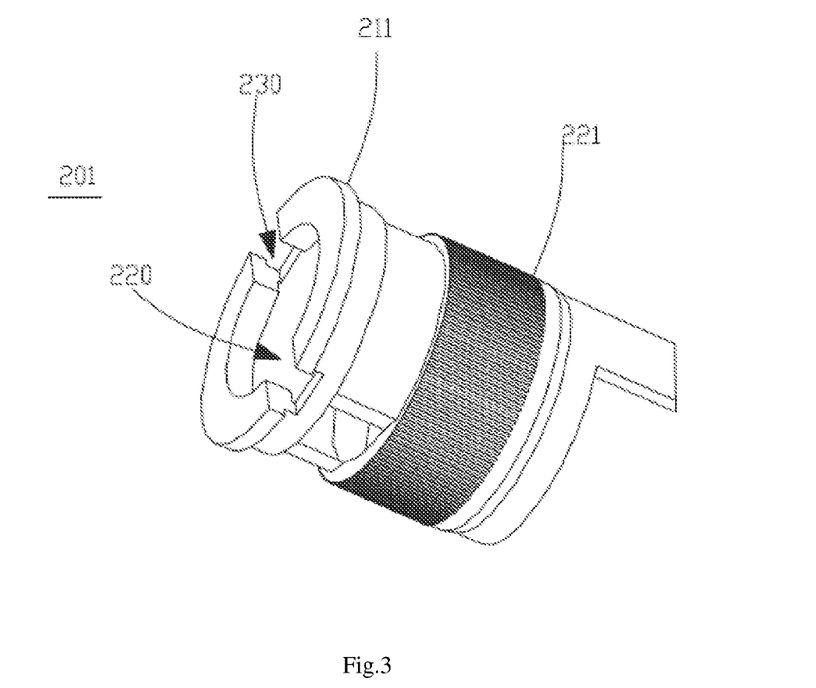
FIG. 3 is a structural schematic view of external battery rod electrode shown in FIG. 2.

As shown in FIG. 3, the second connector is external battery rod electrode 201. The external battery rod electrode 201 is cylindric, hollow inside, comprising a cylindric body 221 and a flange 211 at the end of cylindric body 221 formed circumferentially along the external battery rod electrode 201. The cylindric body 221 inserts into the end of battery sleeve, and permanent connects with battery sleeve in the form of interference fit. The flange 211 abuts on the end surface of battery sleeve, further fastening the external battery rod electrode 201 on the end surface of battery sleeve. Inside hollow of external battery rod electrode 201 forms a butting groove 220, to hold the inserted atomizer electrode assembly. A guide groove 230 which fits the fastener 104 extends in the axial direction of the external battery rod electrode 201 is arranged on the sidewall of the butting groove 220, to guide the atomizer electrode assembly into the butting groove 220, and constantly goes deep into. In this embodiment, the first magnetic member 202 is arranged into the external battery rod electrode 201, and encloses with the internal surface of the external battery rod electrode 201 to form a clamping groove 210 which is used to fasten the fastener 104, the clamping groove 210 is connected with the guide groove 230.

Figure 4:
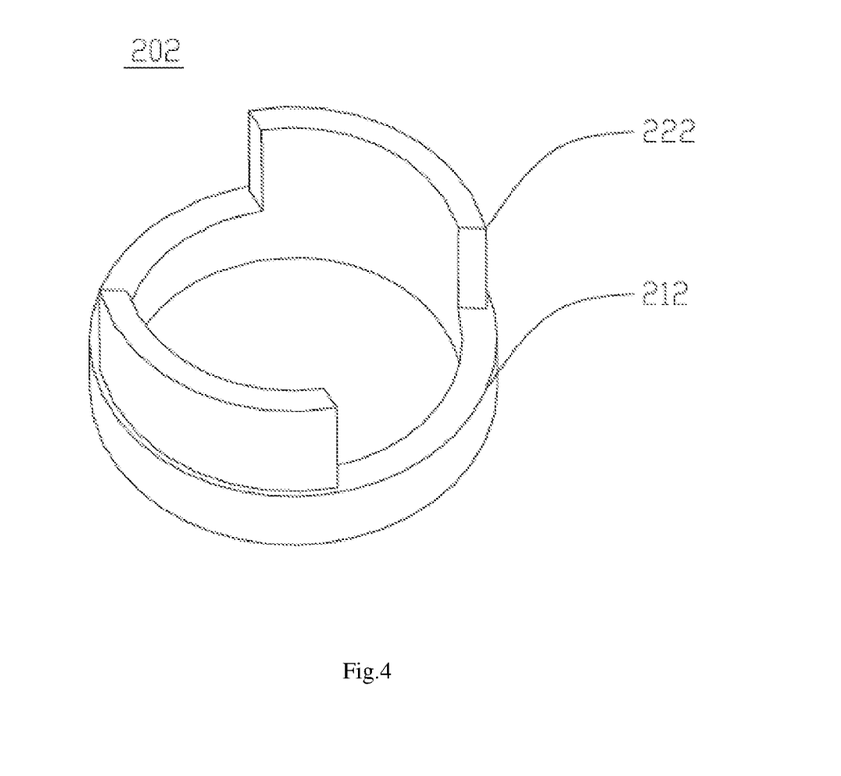
FIG. 4 is a structural schematic view of the first magnetic part shown in FIG. 2.

As shown in FIG. 4, specifically, the first magnetic member 202 is made of magnetic materials such as magnet, iron, or nickel. The first magnetic member 202 is cylindric and hollow inside, comprises a cylindric connection member 212 and a fastening arm 222 formed by axially extending from an end surface of the connection member 212 to the atomizer electrode assembly. When assembling, by inserting the first magnetic member 202 into the inside hollow of external battery rod electrode 201, the connection member 212 permanent connects with the external battery rod electrode 201 in the form of interference fit, the fastening arm 222 abuts the inner surface of the external battery rod electrode 201. In this embodiment, the fastening arm 222 encloses with the internal surface of the external battery rod electrode 201 to form a clamping groove 210. When the atomizer 10 connecting with the battery rod 20, the atomizing electrode assembly is contained in the butting groove 220 of the external battery rod electrode 201, and constantly goes deep into along the guide groove 230, finally goes into the clamping groove 210, thus realizing the connection. Meanwhile, because of the clamping groove 210 is formed by enclosing of the first connector 202, the external atomizer electrode 101 and the first magnetic member 202 attract with each other, to prevent the atomizer 10 from being rotated back because of shock, further avoid the atomizer 10 and battery rod 20 loose to separate, and improves the users' experience.

In other embodiments, the first connector 202 and the external battery rod electrode 201 can use the magnetic material such as magnet, iron and nickel to be integrated, to reduce the assembly steps, and save production time.

Figure 5:
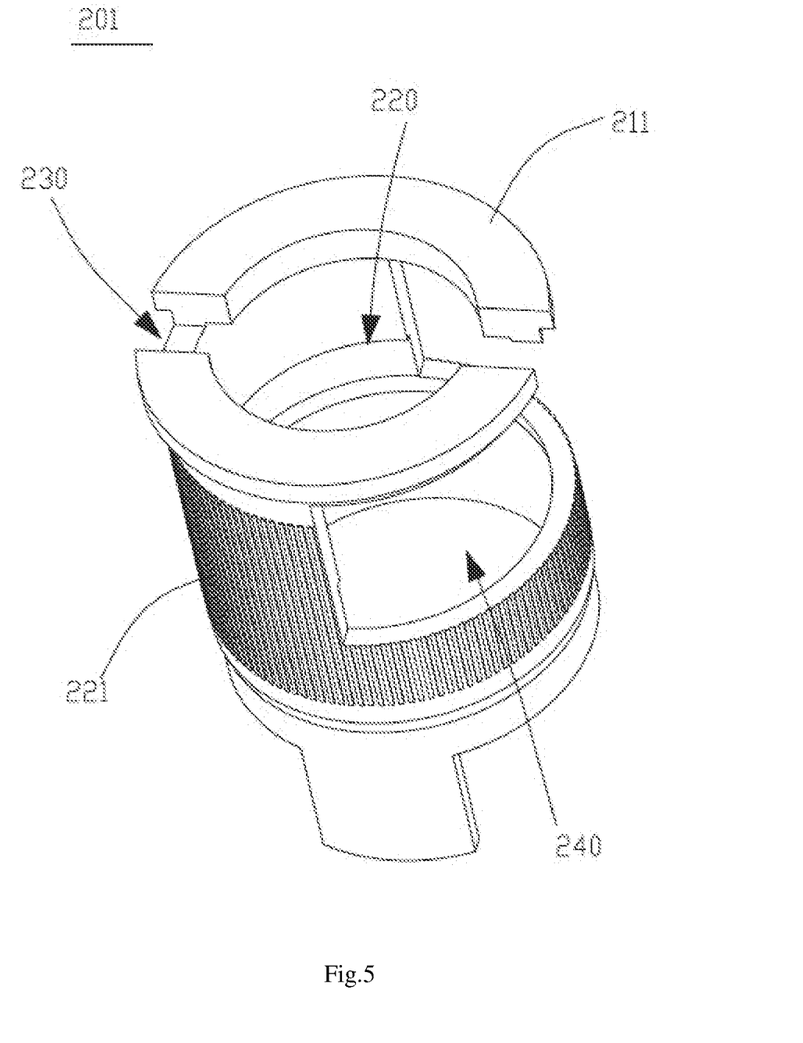
FIG. 5 is a structural schematic view of external battery rod electrode in a second embodiment.
Figure 6:
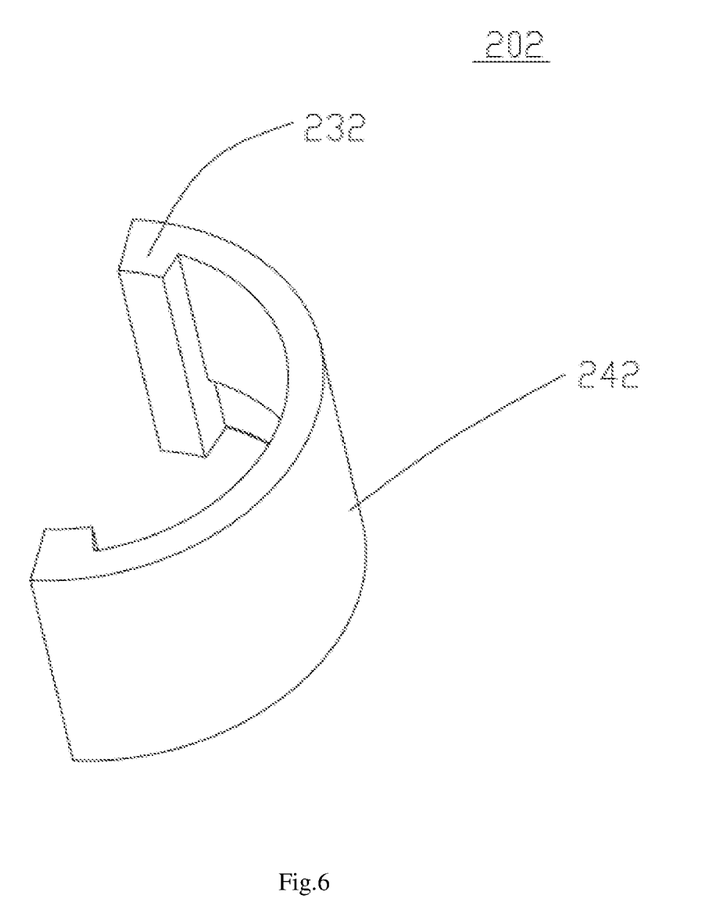
FIG. 6 is a structural schematic view of the first magnetic part in the second embodiment.

As shown in FIG. 5-6, a structural schematic view of external battery rod electrode from one perspective in the second embodiment. The distinction between the first embodiment and the second embodiment merely is: the structure of the external battery rod electrode 201 is different from that of the first connector 202 in this embodiment, but the structures and connection relations of other components and parts of the electronic cigarette are not changed. In this embodiment, The external battery rod electrode 201 is cylindric and hollow inside, comprise a cylindric body 221 and a flange 211 at the end of cylindric body 221 formed circumferentially along the external battery rod electrode 201. The cylindric body 221 is plug-in mounted on the end of battery sleeve, and permanent connects with battery sleeve in the form of interference fit. The flange 211 abuts on the end surface of battery sleeve, to further fasten the external battery rod electrode 201 on the end surface of battery sleeve. Inside hollow of external battery rod electrode 201 forms a butting groove 220, to hold the inserted atomizer electrode assembly. A guide groove 230 which fits the fastener 104 extends in the axial direction of the external battery rod electrode 201 is arranged on the sidewall of the butting groove 220, to guide the atomizer electrode assembly into the butting groove 220, and constantly goes deep into. In this embodiment, an opening 240 is arranged on the cylindric body 221 along circumference direction of the external battery rod electrode, the first magnetic member 202 is clamped into the opening 240, the shape of the first magnetic member 202 is consistent with the shape of the opening 240, so that for better clamping, and does not affect the appearance of the external battery rod electrode 201. The first magnetic member 202 encloses with the internal surface of the external battery rod electrode 201 to form a clamping groove 210 which is used to fasten the fastener 104. The advantage of this structure is: only in the local area of the external battery rod electrode 201 is made of magnetic material, which reduces the amount of magnetic material and save cost.

In this embodiment, the first magnetic member 202 is a curved plate, which comprises curved plate body 242 and two backstop bulges 232. The two ends of curved plate body 242 extend towards each other to form backstop bulge 232. When assembling, the first magnetic member 202 is clamped into the opening 240, the two backstop bulges 232 abut the two ends of the opening 240 respectively. The backstop bulges 232 enclose with the internal surface of the external battery rod electrode 201 to form the clamping groove 210. When the atomizer 10 connecting with the battery rod 20, the atomizing electrode assembly is contained in the butting groove 220 of the external battery rod electrode 201, and constantly goes deep into along the guide groove 230, finally goes into the clamping groove 210, thus realize the connection. Meanwhile, because of the clamping groove 210 is formed by enclosing of the first connector 202, the external atomizer electrode 101 and the first magnetic member 202 attract with each other, to prevent the atomizer 10 from being rotated back because of shock, further avoid the atomizer 10 and battery rod 20 loose to separate, and improves the users' experience.

Figure 7:
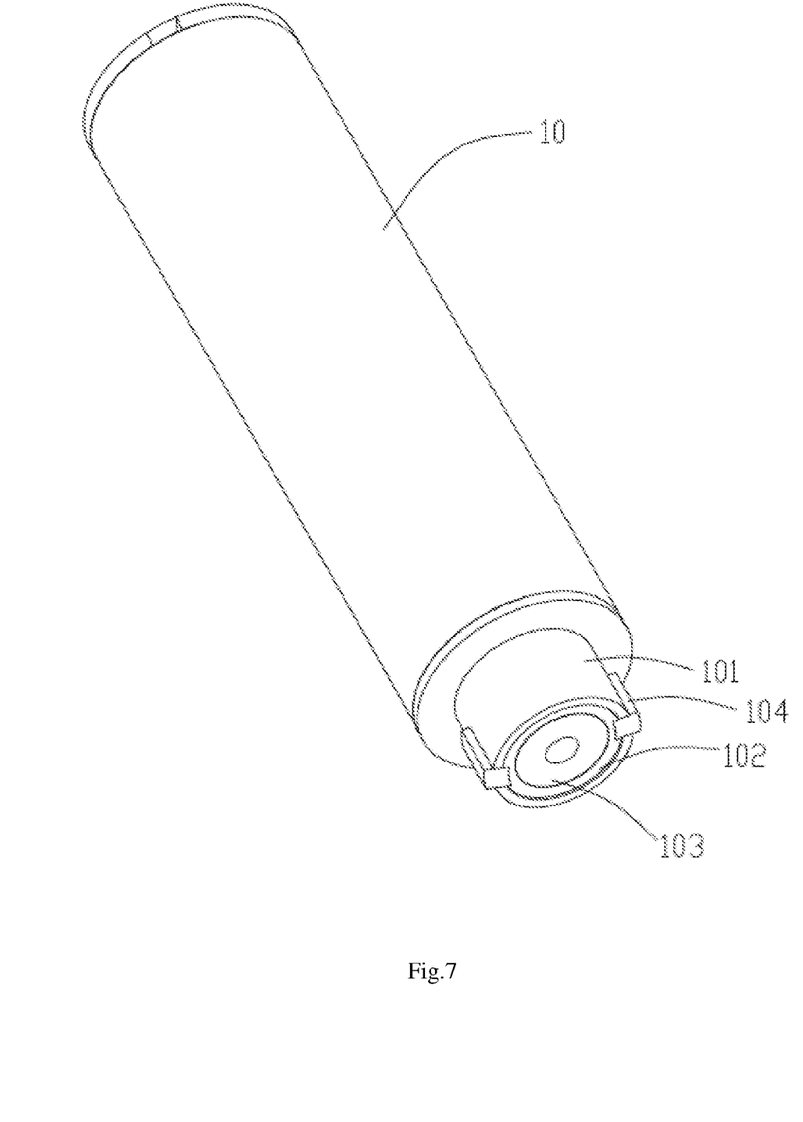
FIG. 7 is a structural schematic view of atomizer in a third embodiment.

As shown in FIG. 7, a structural schematic view of atomizer from one perspective in the third embodiment. The distinction between the third embodiment and the other two embodiments merely is: the structure of the fastener 104 on the provided atomizer 10 is different. Understandably, the structure of the atomizer 10 in this embodiment can also be used in the above-mentioned embodiments. The fastener 104 is arranged on the atomizer insulator ring 102. Specifically, the fastener 104 is a second bulge formed by extending from an outside surface of the atomizer insulator ring 102 towards direction of away from a central axis of the atomizer electrode assembly, and the fastener 104 protrudes from outer surface of the external atomizer electrode 101, which extends to the outer edge of the external atomizer electrode 101. In this embodiment, the fastener 104 and the atomizer insulator ring 102 can be an integrated structure. Understandably, the fastener 104 can be designed as a single bulge, fastening on the atomizer electrode assembly by pasting, welding and other ways, the bulge is made of magnetic materials such as magnet, iron, or nickel.

The atomizer and the battery rod are connected by clamping the fastener of the first connector into the clamping groove of the second connector. At the same time, magnetic members made of magnetic material such as magnet, iron, nickel and cobalt are respectively disposed on the first connector and the second connector, so that the atomizer and battery rod can attract with each other during the connection, thus avoiding the atomizer and battery rod being loose to separate, so that the present invention provides an electronic cigarette which is firm in connection and simple in operation and improves the users' experience.

In the inspiration of the present application, those ordinary skills in the art can also make many modifications without breaking away from the subject of the present application and the protection scope of the claims. All these modifications belong to the protection of the present application.

What is claimed is:

1. An electronic cigarette comprises atomizer (10) and a battery rod (20) which are connected with each other, a first connector and a second connector for connecting the atomizer (10) with the battery rod (20) are arranged at where the atomizer (10) and the battery rod (20) are connected with each other;

wherein a fastener (104) is arranged on the first connector, a butting groove (220) is arranged on the second connector, a guide groove (230) extending in an axial direction of the battery rod (20) and a clamping groove (210) extending in a circumferential direction of the battery rod (20) and communicating with the guide groove (230) are arranged on a sidewall of the butting groove (220), the fastener (104) is clamped into the clamping groove (210); and wherein a first magnetic member (202) is further arranged on the second connector, and a second magnetic member for attracting the first magnetic member (202) so as to prevent the fastener (104) from being rotated back into the guiding groove (230) is further arranged on the first connector;

wherein the atomizer (10) comprises an atomizer electrode assembly, the first connector is the atomizer electrode assembly;

wherein the battery rod (20) comprises an external battery rod electrode (201), the second connector is the external battery rod electrode (201);

wherein the atomizer electrode assembly comprises an external atomizer electrode (101), an inner atomizer electrode (103) which is arranged in the external atomizer electrode (101), and an atomizer insulator ring (102) which is arranged between the external atomizer electrode (101) and the inner atomizer electrode (103);

wherein the second magnetic member is the external atomizer electrode (101);

wherein the first magnetic member (202) is contained in the external battery rod electrode (201), and encloses with an internal surface of the external battery rod electrode (201) to form the clamping groove (210); and wherein the first magnetic member (202) is a hollow cylinder, a fastening arm (222) is formed by axially extending from an end surface of the first magnetic member (202) towards the external atomizer electrode (101)), the fastening arm (222) encloses with the internal surface of the external battery rod electrode (201) to form the clamping groove (210).

2. The electronic cigarette of claim 1, wherein the fastener (104) is a first bulge formed by extending from an outside surface of the external atomizer electrode (101) towards a direction of away from a central axis of the external atomizer electrode (101).

3. The electronic cigarette of claim 1, wherein the first magnetic member (202) and the external battery rod electrode (201) form an integrated structure.

* * * * *